US011182902B2

United States Patent
Husheer

(10) Patent No.: US 11,182,902 B2
(45) Date of Patent: *Nov. 23, 2021

(54) METHOD AND APPARATUS FOR DETERMINING VOLUMETRIC DATA OF A PREDETERMINED ANATOMICAL FEATURE

(71) Applicant: HEARTFELT TECHNOLOGIES LIMITED, Cambridge (GB)

(72) Inventor: Shamus Husheer, Borehamwood (GB)

(73) Assignee: HEARTFELT TECHNOLOGIES LIMITED

( * ) Notice: Subject to any disclaimer, the term of this patent is extended or adjusted under 35 U.S.C. 154(b) by 30 days.

This patent is subject to a terminal disclaimer.

(21) Appl. No.: 16/739,152

(22) Filed: Jan. 10, 2020

(65) Prior Publication Data

US 2020/0175687 A1    Jun. 4, 2020

Related U.S. Application Data

(63) Continuation of application No. 15/757,364, filed as application No. PCT/GB2016/052719 on Sep. 2, 2016, now Pat. No. 10,573,004.

(30) Foreign Application Priority Data

Sep. 3, 2015    (GB) ...................... 1515634

(51) Int. Cl.
G06T 7/00    (2017.01)
G06T 7/62    (2017.01)
(Continued)

(52) U.S. Cl.
CPC .......... *G06T 7/0016* (2013.01); *A61B 5/1073* (2013.01); *A61B 5/1079* (2013.01);
(Continued)

(58) Field of Classification Search
CPC .......... G06T 7/0016; G06T 7/62; G06T 7/50; G06T 7/0012; G06T 7/251; G06T 7/40;
(Continued)

(56) References Cited

U.S. PATENT DOCUMENTS 5,915,386 A    6/1999 Lloyd et al.
10,449,390 B2 *    10/2019 Lachaine ............. A61N 5/1067
(Continued)

FOREIGN PATENT DOCUMENTS

WO    WO/2010/044845 A1    4/2010

OTHER PUBLICATIONS

Lu Guannan et al "A system for limb-volume measurement using 3D models from an infrared depth sensor" 2013 IEEE Symosium on Computational Intelligence in Healthcare and E-Health (CICARE) IEEE. Apr. 16, 2013, pp. 64-69. Abstract figures 1,3,5 sections III.A+B, IV.A.

(Continued)

*Primary Examiner* — Jose L Couso
(74) *Attorney, Agent, or Firm* — Fresh IP PLC; Clifford D. Hyra; Aubrey Y. Chen

(57) ABSTRACT

A method of determining volumetric data of a predetermined anatomical feature is described. The method comprising determining volumetric data of one or more anatomical features present in a field of view of a depth sensing camera apparatus, identifying a predetermined anatomical feature as being present in the field of view of the depth sensing camera apparatus, associating the volumetric data of one of the one or more anatomical features with the identified predetermined anatomical feature, and outputting the volumetric data of the predetermined anatomical feature. An apparatus is also described.

15 Claims, 6 Drawing Sheets

(51) Int. Cl.
*A61B 5/107* (2006.01)
*A61B 5/00* (2006.01)
*G06K 9/00* (2006.01)
*G06T 19/20* (2011.01)

(52) U.S. Cl.
CPC ........ *A61B 5/4878* (2013.01); *G06K 9/00362* (2013.01); *G06T 7/62* (2017.01); *G06T 19/20* (2013.01); *G06T 2207/10028* (2013.01); *G06T 2207/30004* (2013.01); *G06T 2219/2021* (2013.01)

(58) Field of Classification Search
CPC .... G06T 7/60; G06T 7/68; G06T 7/75; G06T 19/20; G06T 19/00; G06T 17/00; G06T 17/20; G06T 5/009; G06T 2207/10028; G06T 2207/30004; G06T 2207/10072; G06T 2207/10081; G06T 2207/20101; G06T 2207/20108; G06T 2207/10136; G06T 2207/30068; G06T 2207/30196; G06T 2219/2021; G06T 2200/04; G06T 2200/08; A61B 5/1073; A61B 5/1079; A61B 5/4878; A61B 5/0002; A61B 5/0064; A61B 5/1077; A61B 5/1072; A61B 5/1074; A61B 5/1075; A61B 5/0077; A61B 5/0537; A61B 5/103; A61B 5/107; A61B 5/418; A61B 5/4312; A61B 5/41; A61B 6/466; A61B 6/502; A61B 8/0858; A61B 2505/06; A61B 2576/00; G06K 9/00362; G06K 9/00201; G06K 9/00214; G06K 9/46; G06K 9/52; G06K 9/00342; G06K 9/00369; G06K 2209/05; G16H 30/40; G16H 30/20; G16H 50/50; G16H 50/20; G16H 20/30; H04N 13/204; G06F 19/321; G06F 19/324
See application file for complete search history.

(56) References Cited

U.S. PATENT DOCUMENTS

| | | | | |
|---|---|---|---|---|
| 2008/0008369 | A1* | 1/2008 | Koptenko | G06T 7/12 382/128 |
| 2008/0319336 | A1 | 12/2008 | Ward | |
| 2009/0096787 | A1* | 4/2009 | Masumoto | G06T 15/08 345/424 |
| 2009/0136106 | A1* | 5/2009 | Roberts | G06T 15/08 382/130 |
| 2010/0074487 | A1* | 3/2010 | Miyamoto | G06T 7/32 382/128 |
| 2010/0166280 | A1* | 7/2010 | Endo | G06T 11/00 382/131 |
| 2010/0172567 | A1 | 7/2010 | Protoski | |
| 2011/0028825 | A1* | 2/2011 | Douglas | G06T 7/0012 600/407 |
| 2011/0216951 | A1* | 9/2011 | Ye | G06T 7/0012 382/128 |
| 2012/0127200 | A1* | 5/2012 | Kohara | G06T 19/00 345/629 |
| 2012/0253170 | A1* | 10/2012 | Kim | G06T 7/149 600/410 |
| 2013/0053679 | A1* | 2/2013 | Owen | A61B 8/4263 600/411 |
| 2013/0057547 | A1* | 3/2013 | Hwang | G06T 7/75 345/420 |
| 2013/0187903 | A1* | 7/2013 | Papageorgiou | G06T 19/00 345/419 |
| 2013/0336550 | A1 | 12/2013 | Kapur | |
| 2014/0046172 | A1* | 2/2014 | Kim | A61B 5/7275 600/411 |
| 2014/0164169 | A1 | 6/2014 | Rusu | |
| 2014/0193056 | A1* | 7/2014 | Neff | G06T 19/00 382/131 |
| 2014/0225887 | A1* | 8/2014 | Aguirre-Valencia | G06T 15/20 345/419 |
| 2014/0294274 | A1* | 10/2014 | Wang | G06T 7/32 382/131 |
| 2015/0043799 | A1* | 2/2015 | Zhan | G06K 9/3233 382/131 |
| 2015/0065859 | A1* | 3/2015 | Hwang | A61B 6/037 600/411 |
| 2015/0157298 | A1* | 6/2015 | Park | A61B 8/466 382/131 |
| 2015/0235364 | A1* | 8/2015 | Aguirre-Valencia | G06T 7/33 382/131 |
| 2015/0294445 | A1* | 10/2015 | Sakaue | A61B 6/469 382/131 |
| 2015/0302894 | A1 | 10/2015 | Boiman | |
| 2015/0348229 | A1* | 12/2015 | Aguirre-Valencia | G06T 19/20 345/419 |
| 2015/0366532 | A1* | 12/2015 | Voigt | A61B 8/463 600/408 |
| 2016/0070878 | A1* | 3/2016 | Soper | G16H 50/50 703/11 |
| 2016/0163048 | A1* | 6/2016 | Yee | G06F 3/04845 382/131 |
| 2016/0171766 | A1* | 6/2016 | Grbic | G06T 7/0016 345/423 |
| 2016/0206203 | A1* | 7/2016 | Yu | G06T 11/008 |
| 2016/0235354 | A1 | 8/2016 | Weiler | |
| 2016/0260208 | A1* | 9/2016 | Rapaka | A61B 6/504 |
| 2016/0292864 | A1* | 10/2016 | Dabbah | A61B 6/486 |
| 2016/0296120 | A1* | 10/2016 | Miyasa | A61B 5/0035 |
| 2017/0213338 | A1* | 7/2017 | Groth | G06T 7/149 |
| 2017/0367645 | A1* | 12/2017 | Klinder | A61B 5/4566 |
| 2017/0367685 | A1* | 12/2017 | Zou | G06T 7/74 |
| 2018/0042322 | A1 | 2/2018 | Weiler | |
| 2018/0137640 | A1 | 5/2018 | Farahbakshian | |
| 2019/0015042 | A1 | 1/2019 | Ettrup | |
| 2019/0029592 | A1 | 1/2019 | Yao | |
| 2019/0122424 | A1 | 4/2019 | Moore | |

OTHER PUBLICATIONS

Juenger M et al: "Beruehrungslose Umfangmessung der Beine—(Touchless legs—volumentry)", Medizinisch Orthopadische Technik, Gentner Verlag. Stuttgart, DE, vol. 126, Jan. 1, 2006, pp. 41-43, XP008164839, Issn: 0340-5508 abstract figure 2 section "Image 3D-System".

M. Hirar et al: "Improvement of a three-dimensional measurement system for the evaluation of food edema" Skin Research and Technology vol. 18, Issue 1, Feb. 24, 2012, pp. 120-124 (Year: 2012).

Yahatjugoda, Channa et al., "Use of a Novel Portable Three-Dimensional Imaging System to Measure Limb Volume and Circumference in Patients with Filarial Lymphedema", American Journal of Tropical Medicine and Hygiene, vol. 97, Issue 6, Dec. 6, 2017, pp. 1836-1842. (Year: 2017).

ISR for International application PCT/GB2016/052719.

* cited by examiner

METHOD AND APPARATUS FOR DETERMINING VOLUMETRIC DATA OF A PREDETERMINED ANATOMICAL FEATURE

This application claims the benefit of U.S. patent application Ser. No. 15/757,364, filed Mar. 4, 2018, which is hereby incorporated by reference in its entirety.

FIELD OF THE DISCLOSURE

The invention relates to a method and an apparatus for determining volumetric data of a predetermined anatomical feature. A non-invasive method and apparatus for monitoring the volume of body parts, or part thereof, of an animal or human is presented, by the application of machine vision techniques to create and compare 3-dimensional (3D) models of the body parts over time. The invention has applicability in the areas of human and animal health, particularly in monitoring the peripheral edema associated with a range of pathologies including heart failure.

BACKGROUND

Water retention resulting from chronic heart failure can be detected by a number of methods, most commonly by measurement a weight gain or an increase in limb volume.

The WHARF study by Goldberg et al. (Am Heart J. Volume 146(4), pages 705 to 712, 2003) demonstrated that compliant patients monitoring their weight on a regular basis could reduce the mortality from chronic heart failure by 50%. Unfortunately, such benefits are not commonly observed in normal patient populations due to non-compliance to a daily regime of weight monitoring, even when internet-connected weighing scales are used to remove any necessity for patients to record or report the information collected.

Brijker et al. (Clinical Physiology, volume 20, issue 1, pages 56 to 61, January 2000) demonstrated that limb volume is a much more sensitive measurement for the purposes of heart failure monitoring than weight gain. Weight measurement has a number of known fluctuations, such as level of hydration and how recently one's bowel has been evacuated that can interfere with the desired signal indicative of excess water retention. The study of Brijker et al. demonstrated that patients showed a change of approximately 5.9% in weight between hospital admission and discharge, compared to a change of 13.1% in leg volume and a change of 7.1% in leg circumference. In addition, the coefficient of variation between weight and leg volume measurement was only r=0.37, suggesting that the two methods are somewhat independent, therefore leg volume monitoring may add significantly to the assessment of edema compared to the measurement of weight alone.

Unfortunately, the clinical gold-standard for limb volume measurement is a water displacement technique that suffers significant inter-operator variation and is cumbersome and error-prone to administer. Essentially, the limb of interest is immersed into a container of water to various depths, and the water displaced from the container is captured and recorded.

Because patients are capable of surviving for many years following the onset of chronic heart failure, the problem of finding a solution to the routine monitoring of changes in limb volume for the casually compliant patient in a home setting is an area of activity.

Therefore, a multitude of devices have been devised to measure changes in limb volume, typically in the form of various "smart" socks or similar, as is described in U.S. Pat. No. 8,827,930B2. The fundamental issue with such approaches is that patient non-compliance is a significant factor in effective long-term monitoring.

An alternative, non-invasive approach is to apply "machine vision" concepts, wherein the limb in question is measured using a 3D imaging system. Hayn et al. applied the Microsoft Kinect depth-measuring camera system to the measurement of leg volume for the detection of edema (AT513091B1). The approach taken by Hayn et al. was to identify a specific set of reference points, lines, curves or planes that had been shown to correlate with limb volume. Unfortunately, this approach provided only modest correlation with weight, and also requires that the patient is oriented in a particular way with respect to the imaging system in order to capture the reference points/lines/curves/planes. This is clearly susceptible to the same compliance issues noted above.

Other approaches to 3D imaging of limbs have been taken, typically in the hospital setting which involves the use of a 3D imaging system for routine measurement of limb volume. Unfortunately, such systems typically require the patient to be rotated with respect to the imaging system, and to have limbs not of interest to be covered so as not to interfere with the observation of the limb of interest. This is clearly not practical for home use.

An alternative approach is described in EP0760622A1, which describes a particularly inexpensive 3D scanner, in which a body part to be digitized is provided with an elastic cover that carries marks to be evaluated by photogrammetry. Overlapping images are taken using one or more roughly positioned cameras, and a 3D model of the body part is generated from the combination of these 2-dimensional (2D) images. Unfortunately, such a system is impractical for home-use by the casually compliant patient as they cannot be expected to diligently wear special clothing.

Stocking-based systems have been the subject of significant academic research, for example Hirai et al. in "*Improvement of a three-dimensional measurement system for the evaluation of foot edema*" (Skin Research and Technology, volume 18, issue 1, pages 120 to 124) and Pratsch et al. in "*Perceived swelling, clinical swelling and manifest lymphoedema—difficulties with the quantifying of leg swellings*" (Phlebologie, volume 41, page 5 to 11, 2012). However, the issue with usability remains significant.

Other methods and devices relating to image analysis are described in U.S. Pat. No. 8,908,928B1, US2011295112A1 and US2015216477A1.

Accordingly, an aim of the present invention is to provide a non-invasive, opportunistic method and apparatus for monitoring the peripheral edema associated with a range of pathologies including heart failure in animals or humans, and reporting the results thereof.

BRIEF DESCRIPTION OF THE DRAWINGS

The present disclosure can be understood with reference to the description of the embodiments set out below, in conjunction with the appended drawings in which.

DETAILED DESCRIPTION

Figure 1:
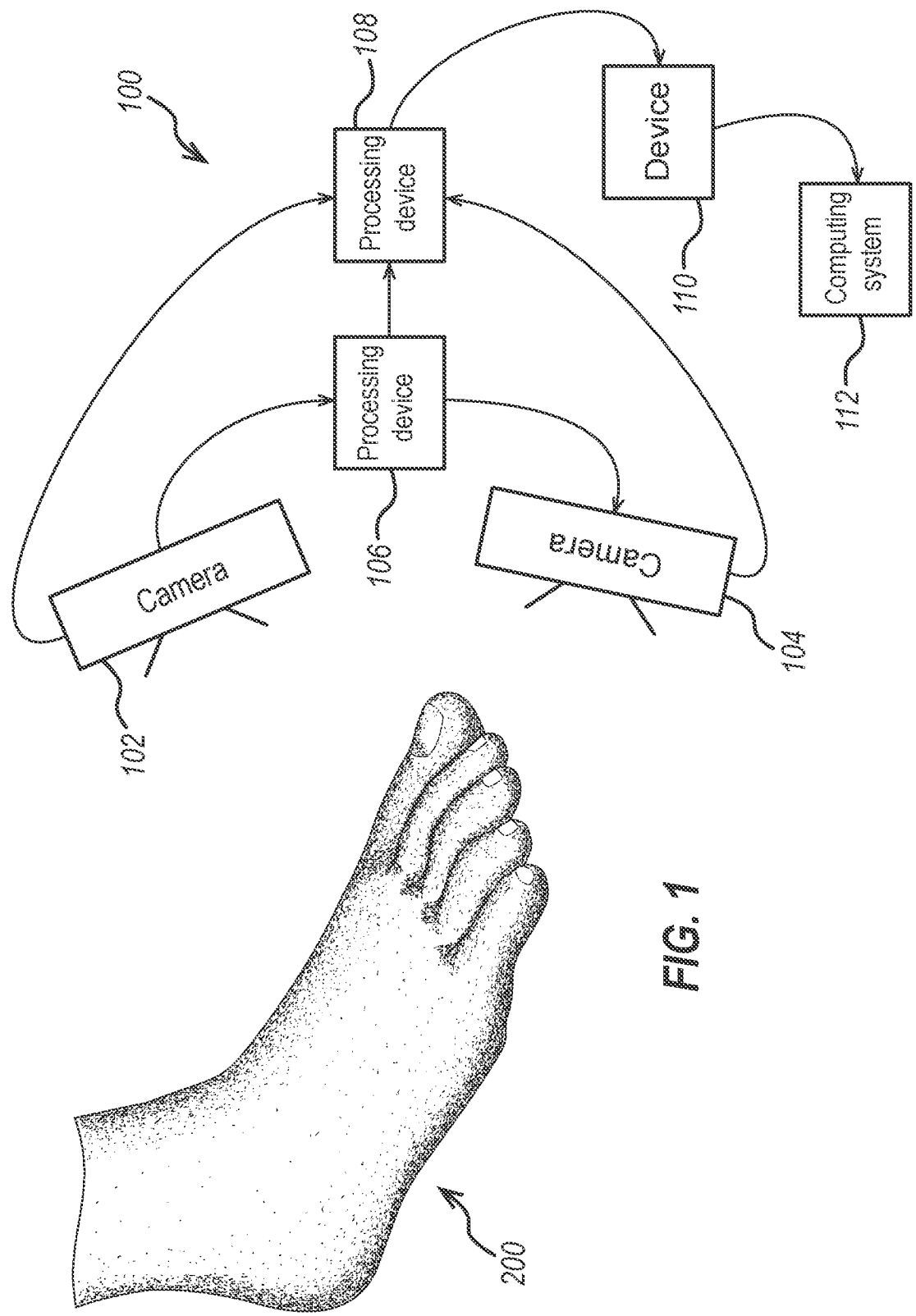
FIG. 1 illustrates an apparatus according to an embodiment of the invention.

According to a first aspect of the invention there is provided a method of determining volumetric data of a predetermined anatomical feature, the method comprising: determining volumetric data of one or more anatomical features present in a field of view of a depth sensing camera apparatus, identifying a predetermined anatomical feature as being present in the field of view of the depth sensing camera apparatus, associating the volumetric data of one of the one or more anatomical features with the identified predetermined anatomical feature, and outputting the volumetric data of the predetermined anatomical feature.

The step of identifying a predetermined anatomical feature as being present in a field of view of the depth sensing camera apparatus may be performed before the step of determining volumetric data of one or more anatomical features present in the field of view of the depth sensing camera apparatus.

Upon identification of the predetermined anatomical feature being present in the field of view of the depth camera apparatus, the method may comprise obtaining three-dimensional data of the predetermined anatomical feature and determining the volumetric data of the predetermined anatomical feature based on the three-dimensional data.

The method may comprise acquiring a two-dimensional image from the depth sensing camera apparatus and identifying the predetermined anatomical feature as being present in a field of view of the depth sensing camera apparatus in accordance with the two-dimensional image.

The step of identifying a predetermined anatomical feature as being present in a field of view of the depth sensing camera apparatus may be performed after the step of determining volumetric data of one or more anatomical features present in the field of view of the depth sensing camera apparatus.

The method may comprise obtaining three-dimensional data of the one or more anatomical features and determining the volumetric data of the one or more anatomical features based on the three-dimensional data.

The volumetric data of one of the one or more features may be associated with the identified predetermined anatomical feature by comparing the volumetric data of each of the one or more anatomical features with a three-dimensional representation of a predetermined anatomical feature, and identifying one of the one or more anatomical features as being the predetermined anatomical feature.

The step of determining the volumetric data may comprise processing the three-dimensional data in dependence on a three-dimensional representation of the predetermined anatomical feature.

The three-dimensional representation of the predetermined anatomical feature may be a deformable three-dimensional model, and wherein the method may comprise parametrically deforming the three-dimensional model to fit the three-dimensional data of the predetermined anatomical feature.

The three-dimensional model may be deformed by one or more of rotation, altering a joint angle and volumetric change.

The three-dimensional representation of the predetermined anatomical feature may be a deformable three-dimensional model, and wherein the method may comprise deforming the three-dimensional data of the predetermined anatomical feature to fit the three-dimensional model.

The three-dimensional data may comprise multiple data sets of anatomical features at different orientations.

The data may be periodically or continuously received from the depth sensing camera apparatus.

The three-dimensional data may comprise three-dimensional image data.

The three-dimensional data may represent at least one partial representation of the predetermined anatomical feature.

The predetermined anatomical feature may be a limb, and may be a foot.

The depth sensing camera apparatus may comprise at least one emitter and one detector array, or at least two detector arrays.

The method may comprise recording the time at which three-dimensional data is captured, and wherein the volumetric data may be generated in dependence on the recorded time.

According to a second aspect of the invention there is provided a method of determining volumetric data of a predetermined anatomical feature, the method comprising: identifying a predetermined anatomical feature as being present in the field of view of the depth sensing camera apparatus, determining volumetric data of one or more anatomical features present in a field of view of a depth sensing camera apparatus, associating the volumetric data of one of the one or more anatomical features with the identified predetermined anatomical feature, and outputting the volumetric data of the predetermined anatomical feature.

According to a third aspect of the invention there is provided a system comprising: a depth sensing camera apparatus; and a processor coupled to the depth sensing camera apparatus; wherein the processor is configured to perform any of the methods described above. The depth sensing camera apparatus may comprise at least one emitter and one detector array, or at least two detector arrays.

According to a fourth aspect of the invention there is provided a computer readable medium having stored thereon instructions which, when executed on a processor, cause the processor to perform any of the methods described above.

FIG. 1 illustrates an apparatus 100 according to an embodiment of the invention. The apparatus 100 or system includes a depth sensing camera apparatus. The camera apparatus in this embodiment includes two infra-red and visible light sensitive cameras 102, 104. Each camera 102, 104 also includes a controlled infra-red (IR) emitter. Accordingly, the apparatus 100 may continuously observe an imaging volume or field of view without disturbing a patient. In the preferred embodiment, the depth sensing cameras are both IR and visible light sensitive, such that controlling the IR emitter allows the imaging system to capture at least IR images and 3D data. If visible lighting is sufficient, the camera may also be used to capture visible color information. This arrangement has the benefit of not disturbing the patient, whilst capturing color information when possible. Color information may be a useful adjunct to limb volume information when a medical professional is assessing a possible edema.

It will be appreciated that the camera apparatus may include at least one infra-red sensitive camera, and at least one controlled light projector (e.g. infra-red emitter or laser), or at least two spaced apart conventional cameras (i.e. cameras containing a single 2D imaging array.

The apparatus 100 further includes a processing device 106 which receives image data, in this example 2D image data, from the camera 102. The processing device 106 is configured to identify if a limb of interest (e.g. foot 200) is present within the 3D environment imaged by the camera 102, for example. The processing device 106 includes 2D image analysis software or hardware, which is capable of identifying a predetermined limb from a 2D image. The analysis software or hardware utilizes similar algorithms to those used for face recognition. For example, elements of the limb are identified by extracting landmarks, or features, from a previously acquired image of the patient's limb. An algorithm is consequently used to analyze the relative position, size, and/or shape of elements of the limb (e.g. toes, ankle and heel of a foot 200), and these elements are used to search a 2D image. Radio tagging of the limb of interest may also be used to more easily identify if the limb of interest is in the field of view or imaging environment of the camera 102. The processing device 106 is configured to trigger the acquisition of 3D image data from the cameras 102, 104, when the patient's limb is identified as being present in the field of view of the camera 102. The 3D image data are acquired by a processing device 108.

The processing device 108 acquires the image data from the depth sensing camera apparatus 102, 104, and is configured to extract volumetric information about the patient's limb. The volumetric data is subsequently passed or transferred to a device 110, for reporting. The device 110 is a personal computing device and includes a user interface (e.g. screen/monitor and an input device) for allowing a user to visualize the volumetric data. The device 110 in this example is located in the same location as the depth sensing camera apparatus, and is configured to communicate over the Internet, including a GSM network, or an intranet, for example, with a remotely located computing system 112 or cloud computing system. The processing device 108, may also communicate directly with the remotely located computing system 112, such that computing system 110 is not required. The remotely located computing system 112 may be accessible by a medical practitioner or other care worker.

In this example each of the processing devices 106, 108 includes a processor capable of launching and running software programs (e.g., applications) stored in a memory (e.g., RAM and/or ROM), and an input/output interface configured to communicate with each other, the depth sensing camera system 102, 104 and the computing device 110 and/or the computing system 112. It will be appreciated that the two processing devices 106, 108 could be provided as a single device, and may include one or more applications or software programs, or may include one or more application specific integrated circuits. In this regard, the processing devices 106, 108, may be packaged together with the depth sensing camera system 102, 104 in a single vendible unit, which is configured to communicate with the computing device 110 or the remotely located computing system 112. Such a single vendible unit may also include a user interface (e.g. a touch sensitive display/touch-sensitive overlay on a display). Each of the depth sensing camera system and processing devices 106, 108, 110 may also include a short-range, wireless communication system and may include a wireless bus protocol compliant communication mechanism such as a Bluetooth® communication module to provide for communication with similarly-enabled systems and devices or IEEE 802.11 radio standards, which is more typically known as WiFi.

The method which is performed by the apparatus 100 illustrated in FIG. 1 is now described in associated with FIGS. 2 to 10.

The depth sensing camera apparatus 102, 104 is arranged within the home environment of a patient, in such a manner that opportunistic images of the feet/legs are likely to be observed. It has been found that locating the depth sensing camera apparatus 102, 104 near the bed to scan the area from which the patient is likely to get into bed and/or get out of bed, is particularly advantageous as there are few other times when patients will typically have exposed feet/legs without footwear, socks etc. Furthermore, it has been found that a horizontal arrangement of cameras inside a bar-like enclosure is suitable for attachment to a wall at a distance of approximately 70 cm (i.e. a distance in the range of 50 cm to 100 cm) from the floor and 1 m from the bed, with a distance between cameras of 100 mm in this example. Other arrangements and positions of cameras are contemplated. For example, near an access point to a shower or bath area. Alternative arrangements include, for example, a semi-circle of cameras around an imaging volume. Although preferable for image collection such a semi-circular arrangement may be considered to be more obtrusive in the patient's environment.

The depth sensing camera system optionally includes the facility to automatically adjust various lighting conditions, without affecting the patient. Preferably this is performed through the use of color cameras without infra-red filters, such that in low-light conditions an infrared LED can be used to provide IR light. The depth sensing camera system is configured to dynamically adjust the IR LED power to provide optimal lighting conditions for monitoring the scene, as is known in the art.

The processing device 106 is configured to receive image data form camera 102 and to monitor the environment or field of view of the camera 102 for the object of interest (i.e. a patient's foot 200). This is achieved continuously, by capture and video analysis, or periodically, e.g. once per second. Video analysis (i.e. continuously) is preferred, since the capture of 3D image data can be triggered when the feature or object recognition has determined that a foot is present in the field of view or environment of the depth sensing camera apparatus, and the foot is determined not to be moving too fast (e.g. less than 100 mm/s) through the environment viewed by the depth sensing camera apparatus. If the foot is moving faster than 100 mm/s, motion blur may be introduced into the 2D images and depth artefacts may be introduced into the 3D image data. The speed of the foot may be determined by measurement of the distance the foot has moved in between video frames, for example. However, video speed recognition may impact limitations on the amount of processing that can be performed for the foot recognition. Therefore, it is preferable to opportunistically trigger the collection of 3D image data on the basis of a fast estimate that a foot may be present, and later discard any data image if it is determined that the foot of interest is not in fact present. Once a foot has been optimistically recognized, and optionally determined to be moving slowly enough to collect robust 3D image data, a 3D measurement is triggered. It is also preferable to match an imaged foot against a set of target feet (i.e. multiple matches) to minimize false-triggering on feet that do not belong to the patient.

The 3D measurement includes collecting or acquiring at processing device 108 images from the cameras 102, 104 of the depth sensing apparatus 100, which are focused on the imaging volume or field of view. In this example two cameras are used but from different locations. The trigonometric relationship between the scene observed or environment observed by each camera (or projected by each projector) enables a calculation of the distance from each camera or projector. This relationship allows one to calculate the maximum depth resolution that is possible for a given set of cameras and projectors, which is a function of the separation between the cameras/projectors (which in this example is 100 mm), the separation between the cameras/projectors and the target being measured (which in this example is 1 m), and the angular resolution of each pixel in the cameras/projectors, which is a function of the camera/projector optics and the physical size of each pixel. Software used for such 3D analysis is commonly referred to as "3D reconstruction", "Multi-View Stereo" or "Structure from Motion" software, which typically either matches pixels between cameras/projectors to work out the 3D distance to the target, or builds a 3D simulation of the target that best matches the observations made (i.e. either solving a matching problem or optimizing the inverse problem). This analysis may be further refined using techniques of "Structure from Shading" where the detail of a surface can be reconstructed from 2D images collected given some assumptions about the lighting present in the scene.

The 3D data or measurement comprises multiple, preferably high-resolution, images taken in succession from the sensor array of each of the cameras 102, 104. The images from each camera are typically synchronized in time, to avoid artefacts due to motion within the scene. This is done to reduce the depth-uncertainty due to the timing-uncertainty in triggering for a maximum rate of movement in the scene. For example, if two cameras 100 mm apart with angular resolution of 0.02 degrees per pixel are configured to monitor a scene 1000 mm away from the cameras, the depth (z) resolution will be of the order of 5 mm for a 1-pixel uncertainty between cameras. The (x,y) resolution of each pixel in each camera is therefore of the order of 0.5 mm. Accordingly, a 0.5 mm uncertainty in position across the image due to movement combined with camera synchronization error will correspond to approximately a 5 mm error in depth perception. If a foot during a slow walk, whilst standing on the floor but having a foot-to-leg angle change, is assumed to move at 100 mm/sec, then timing jitter should be kept below 5 msec (i.e. 0.5/100), and preferably much less than this. This can be achieved using electronically synchronized systems.

It is preferable to assist later stereoscopic matching algorithms, if the depth sensing camera apparatus does not contain a known light projector, by at least configuring the apparatus to control a "texture projecting" light source, which projects a pattern of IR light over the scene so that objects of uniform color have at least some texture projected onto them. It is also preferable, if the camera is IR-sensitive, to take measurements at multiple levels of IR lighting such that extrapolation to zero IR lighting is possible in order to extract visible color information from the camera more reliably. This visible color information may be useful to medical professionals in visually assessing a possible edema that the system identifies. Color information is also useful in the assessment of wound healing, for which 3D and color information is a particularly useful combination. Therefore, the 3D image capture process preferably includes a series of synchronized images taken from multiple cameras with various levels of IR illumination and IR texture projection applied.

Once 3D image data has been collected by processing device 108, the data is processed by a quality-estimation algorithm at the processing device 108 to determine the likelihood of good quality data resulting from the subsequent processing stages. If it is determined that the image data is likely to give rise to a good result, the image data are entered in to a queue in the memory of processing device 108 for processing, with the data having the highest anticipated good result first. For example, an anticipated good result will be expected from an image set where the foot is approximately centrally located in the imaging volume, is moving slowly, is not occluded by other objects in the scene, and the foot orientation is not very similar (i.e. is dissimilar) to other recently acquired samples. This is beneficial, since the applicant has found that once a patient is observed by the system once, it is more likely that the patient will be observed multiple times within a short period of time (e.g. they are walking around a room). The system then allows for prioritization of the "best" data, as well as data from the greatest range of orientations observed, if there is limited storage space or processing time available within the system, and in cases of resource constraints (e.g. storage space or time) can allow for expected poor image sets to be deleted prior to full processing. The use of a queue ensures that the combination of temporary storage space and processing time is optimally used, with the queue generally never emptying completely (i.e. the predicted lowest-quality data never actually gets processed, it is discarded by the arrival of newer high-quality data that causes the queue to overflow). This queue system located in the memory of the processing device 108 can be expanded to multiple queues if, for example, while the full quality-estimation is performed, more image data may be acquired. For example a first queue might be based on 2D image quality and positive recognition of the patient's foot rather than those of other occupants of a house, and a second prioritization queue might be based on incorporating 3D processing to help prioritize a wide range of orientations of the foot to the imaging system.

Figure 2:
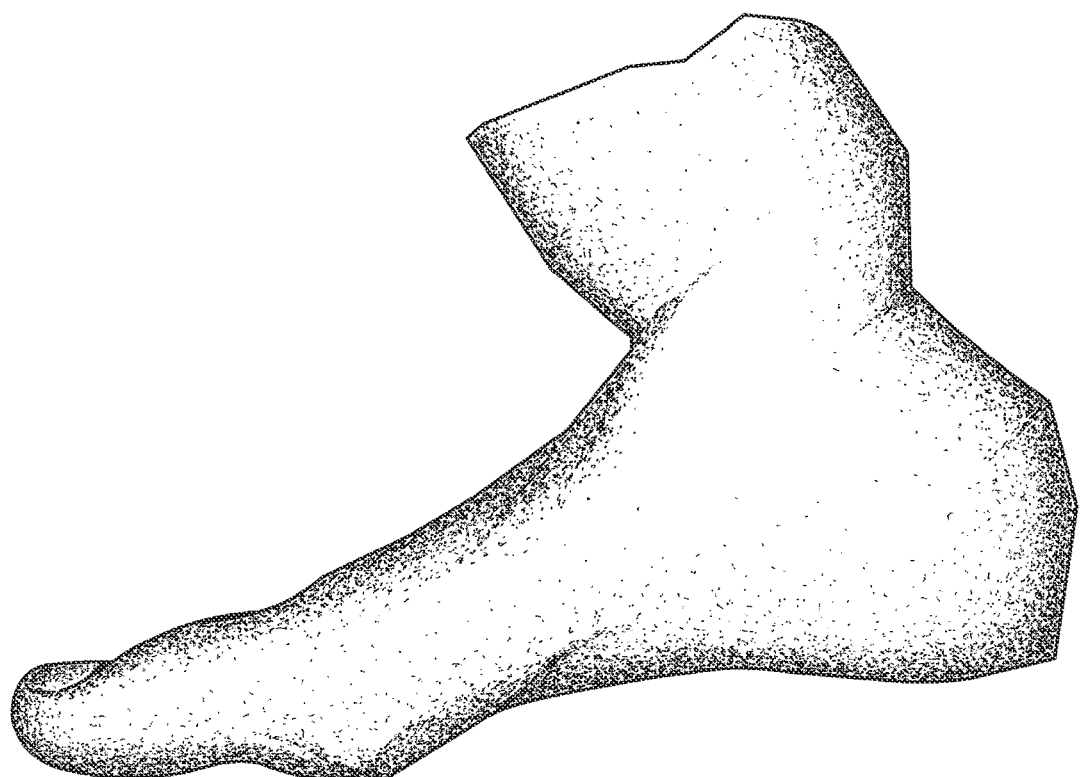
FIG. 2 illustrates 3D image data of a foot as it is observed by a depth sensing camera apparatus.

Image data are retrieved from the top of the queue and a point cloud (i.e. 3D data) is generated by the processing device 108 using a 3D reconstruction algorithm, as is known the art. The 3D image data for each acquisition or exposure is derived from at least two images, either from the two separate cameras, or from one projector and at least one camera. A summary of several such algorithms is provided by D. Scharstein and R. Szeliski, "A taxonomy and evaluation of dense two-frame stereo correspondence algorithms" (International Journal of Computer Vision, 47(1/2/3), page 7 to 42, April-June 2002). The processing device 108 also performs various image processing functions on the image data, for example, rectification, and also on the point cloud 3D data, for example, noise removal. The point cloud 3D data may be further processed to remove background artefacts. FIG. 2 illustrates an example of the 3D image data of a foot as it is observed by the depth sensing camera apparatus 102, 104.

Figure 3:
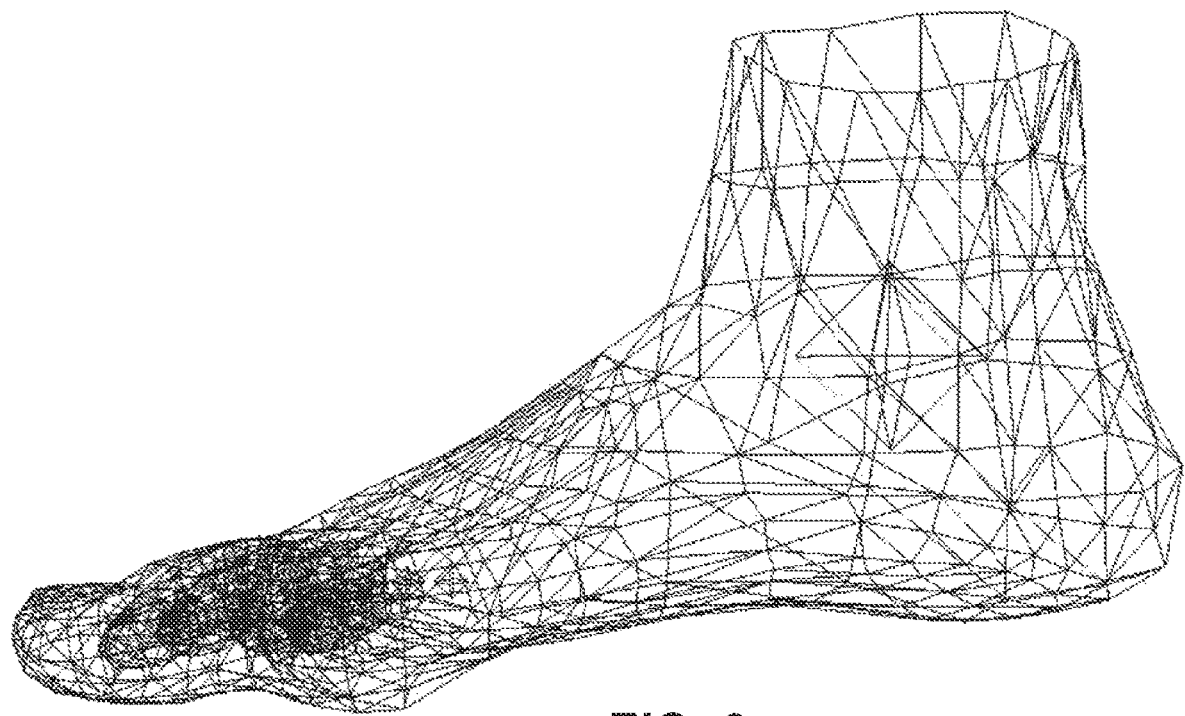
FIG. 3 illustrates an example of a reference 3D model of a foot.

The point cloud 3D data is then used in association with a 3D model of a foot in order to fit the 3D model to the point cloud 3D data. The limb of interest is identified using the same 2D recognition used to identify the foot previously, or a separate 3D recognition method is used, as is known in the art. FIG. 3 illustrates an example of a reference 3D model of a foot. This is achieved by parametrically adjusting the 3D model until a good match is found between the 3D model and the point cloud 3D data. For example, the well-known iterative closest point method may be used whereby a random selection of points from the point cloud 3D data are matched to their closest points in the 3D model, whilst the parameters of the model are adjusted, to find the best set of model parameters (e.g. orientation, joint angles, volumetric distortions and so on). This is repeated using different random samplings so that the impact of outlier points is minimized, until a good match between the 3D model and the observed data is found (i.e. this is repeated until a match with the lowest error is found). For example, the original 3D reference model may be oriented with the left side of the foot facing the camera, a leg-to-foot angle of 90 degrees, and a lower leg represented by a cylinder having a circumference of 30 cm and a height from the floor of 25 cm. The best fit of the 3D model to the point cloud 3D data, in this example, is with the foot facing the camera front on, with an 80 degree foot-to-leg angle and a 33 cm lower-leg circumference. If a good match cannot be achieved, the 3D image data is discarded, and the process is started again using the next set of 3D image data from the queue. It will be apparent that at least two images are used to generate the point cloud, and these two images represent three-dimensional image data, but more than two images may be used.

The 3D reference model may be modified to exclude regions that are particularly variable or problematic to measure, such that measurement precision of the modelled regions is improved. For example, the toes on the foot consist of a large number of joints that may be at a range of relative orientations, as well as a number of regions between toes that are difficult to measure effectively during any one observation. Therefore a reference 3D model of a foot may be truncated a certain distance from the back of the foot, in order to exclude this high-noise region from calculations of foot volume for edema monitoring purposes. For example the front 5 cm of the foot may be cut from the 3D model to remove the toes and complex joints surrounding the toes, since fitting so many parameters may be challenging and not relevant when determining the changes in the volume of the foot.

Figure 4:
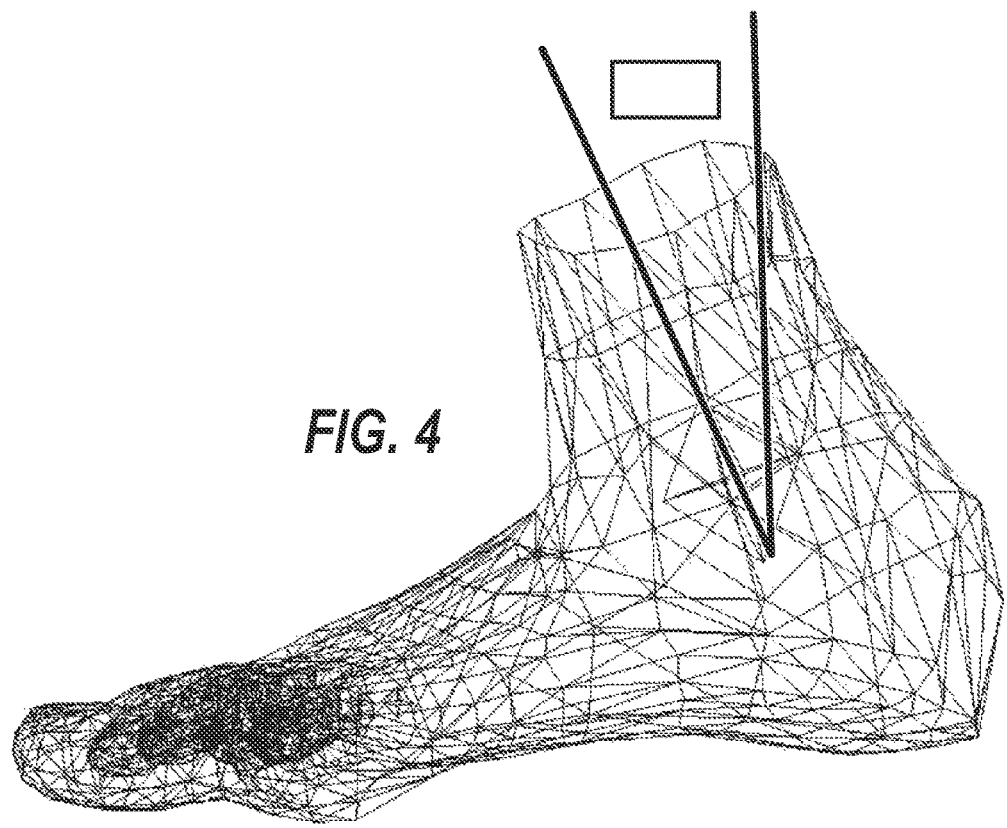
FIG. 4 illustrates a 3D model after adjustment of a parameter for a leg-to-foot-angle has been performed.
Figure 5:
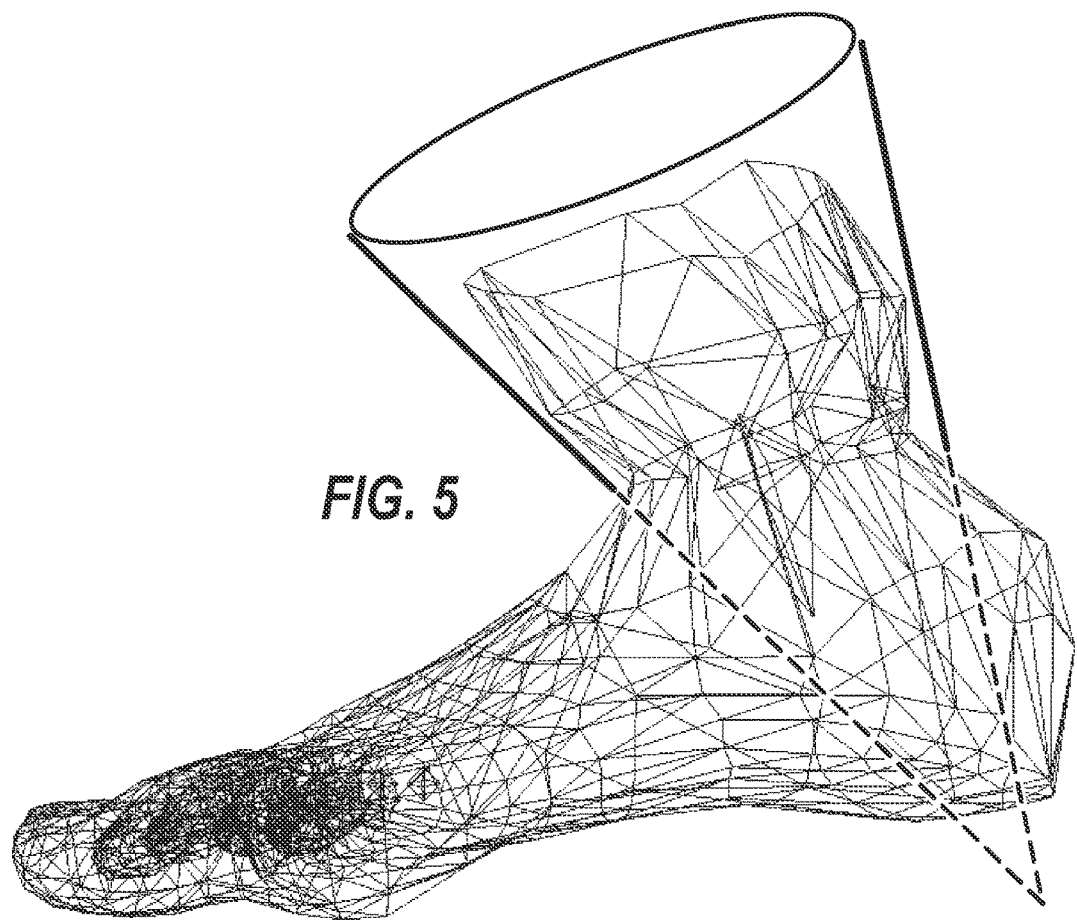
FIG. 5 illustrates the 3D model after adjustment of a second parameter for lower-leg-conical-volume.
Figure 6:
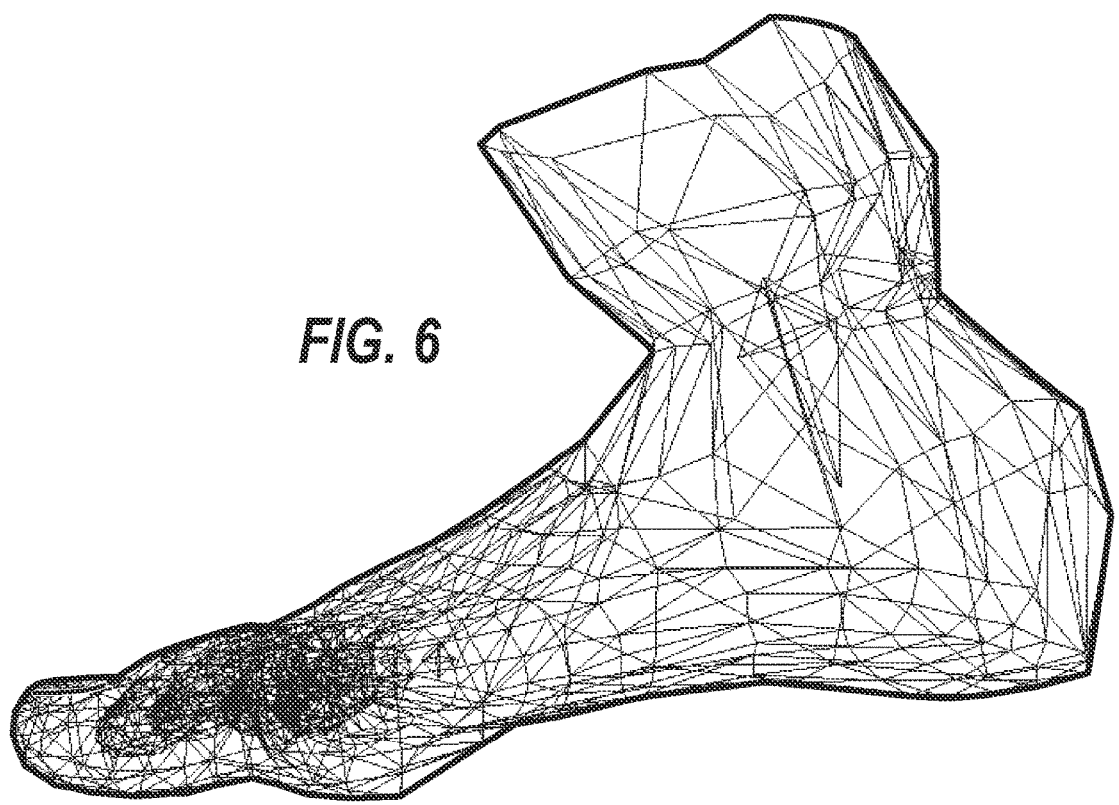
FIG. 6 illustrates the resulting model which more closely matches observed 3D data.

FIG. 4 illustrates the 3D model after adjustment of a parameter for leg-to-foot-angle has been performed. FIG. 5 illustrates the 3D model after adjustment of a second parameter for lower-leg-conical-volume. The resulting model is illustrated in FIG. 6 which more closely matches the observed 3D data and allows a calculation of 3D volume data with respect to the reference model to be calculated. For example the change in volume due to the lower-leg-conical-volume is determined without any impact from the change in leg-to-foot-angle, as is discussed below.

The distorted 3D model is subsequently modified by the processing device 10 to reverse or dis-apply non-volumetric distortions which were performed when matching the 3D model to the point cloud 3D data. For example, the 80-degree foot-to-leg angle is transformed or reversed back to 90-degree foot-to-leg angle, but the lower leg circumference of the 3D model which was matched to the point cloud 3D data is retained. Accordingly, volume-relevant changes are maintained, and the 3D model is otherwise returned to its reference state.

The processing device 108 integrates the volume-matched model over a specified region, for example, at each 1 mm portion from the floor or bottom of the 3D model in the illustrated orientation. In this manner, the distortable model provides a consistent mechanism to obtain volume data as though the foot were in a reference orientation, even allowing the arbitrary orientations and joint angles that are observed when opportunistic data is collected. Thus, volumetric data in the form of a volume of the observed limb, or feature is are obtained.

The source images (2D and 3D images) may be "masked" to blank out pixels that are not relevant for fitting with the foot model, for example, pixels that might correspond to other objects in the patient's environment. This is done for patient privacy should these images be transmitted to any care workers.

The resulting foot model parameters and calculated volume, as well as the masked images, are then transmitted to a cloud service where alarms can be triggered for care workers if a concerning trend in volume change is observed. A care worker may then inspect the relevant images and/or foot models in order to assess the severity and urgency of the case, and proceed with a care pathway. As describe above, the processing device 108 may output the resulting data to a local computing device 110, which subsequently transmits the data to an external device 112 such as a cloud service, using an Internet or intranet connection.

The method and apparatus have been described for a cycle of image capture and analysis. However, it will be appreciate that the process of fitting the 3D model to the image data may be repeated periodically so as to generate a profile of volume data against time. This profile may be transmitted to a practitioner or care worker. The process may be performed periodically (e.g. once a day, week or month), or may be performed every time that the capture of 3D image data is triggered. For example, the processing device 108 may include a pre-stored schedule, which may trigger the capture of images, or may trigger the image processing based on opportunistically acquired images. The schedule may be once a day, once a week, or once of month, or any other period specified by a practitioner. Therefore, the invention provides a monitoring and reporting system and method.

The generation of the initial 3D foot model upon which processing is based is now described. This may be collected in a number of ways, either using a separate reference scanning system (e.g. 3D laser scanner, or MRI scanner), or by having the patient perform a series of 3D image captures under known conditions using the same hardware described above. In either case, the resulting full limb 3D data, taken at multiple orientations and joint angles, is used to generate a parametrically distortable model for later processing. The parametrically distortable model is designed such that it matches as well as is practicable to the full limb 3D image data at multiple orientations and joint angles, without implying any change in the overall volume of the foot. This may be achieved either by generating an accurate multi-parameter model including all of the relevant joints, muscles, and so on, or by using a simpler parametric model and including a set of "volume cancelling" terms within the model. For example, it has been found that if the model systematically underestimates total volume as the leg-to-foot angle increases, a "volume cancelling" term may be applied to increase the apparent volume in accordance with the leg-to-foot angle observed.

It will be appreciated that over time, the patient's body may adjust in ways that lead to the reference 3D model becoming systematically unrepresentative, for example, as a result of diet or exercise. Therefore, the initial reference 3D data at a wide range of orientations and joint angles can be combined with the 3D data collected over time to yield a slowly self-adjusting reference 3D model. This may not be suitable for some application areas where subtle changes in absolute volume over long time-periods are important, but for edema monitoring for heart failure patients the change in volume that is clinically relevant is of the order of 10% over two weeks. Therefore a self-adjusting model with a time-period of months should not negatively impact on edema assessment, whilst ensuring that the model remains relevant over extended periods of time and avoiding the need for periodic re-calibration. Accordingly, it is preferable to update the 3D model periodically when a new reference model becomes available, for example as the result of a full scan of the limb in question. Alternatively, the 3D model is incrementally updated over time.

The use of a deformable 3D model as the reference to which captured data is compared during any one measurement is advantageous when applied to time-series collection of data in an opportunistic fashion, as in the present invention. Although any one collected set of 3D image data can be mapped onto the 3D model, any one set of 3D image data is highly unlikely to describe all of the changes between the 3D reference model and the current state of the limb under consideration. For example, the imaging system may only capture 3D data about the side of the limb facing the depth sensing camera apparatus, if the depth sensing camera apparatus does not cover a full 360 degree circumference (or full solid-angle of a sphere). However, over time a series of such opportunistically collected 3D image data is likely to describe all, or broadly all, of the surfaces of the 3D reference model. The reference 3D model can therefore be updated over time from this time-series. For example, as the patient moves around their environment, the limb under consideration may be observed by the imaging system over a range of orientations, allowing the reference 3D model to be evolved over time. Preferably, regions of the 3D model are only updated using data that have passed pre-defined quality and consistency checks, for example having observed the same consistent discrepancy between the observed data and the 3D reference model over at least a certain number of observations separated in time by at least a certain period. In this way, for example, the "texture" of a 3D model might be automatically updated after a patient gets a tattoo, and the system determines that this is not some temporary change in skin complexion.

It has been reported that limb volume may alter depending on recent history, e.g. if the patient has been sleeping horizontally just before measurement, vs standing vertically. Therefore, the apparatus may also record the time at which the images are captured and this temporal data may be output along with the volumetric data/profile. Furthermore, this temporal data may be used as an input to the 3D distortable model in order to compensate for the time at which the images are captured. For example, if the apparatus regularly captures a user effectively getting out of bed in the morning, vs getting into bed in the evening, the processing device 110 may construct a model of this typical variation over several days of measurements, or may use this temporal data to further distort the 3D distortable/deformable model to compensate for the time of day at which the 3D images are captured.

Figure 7:
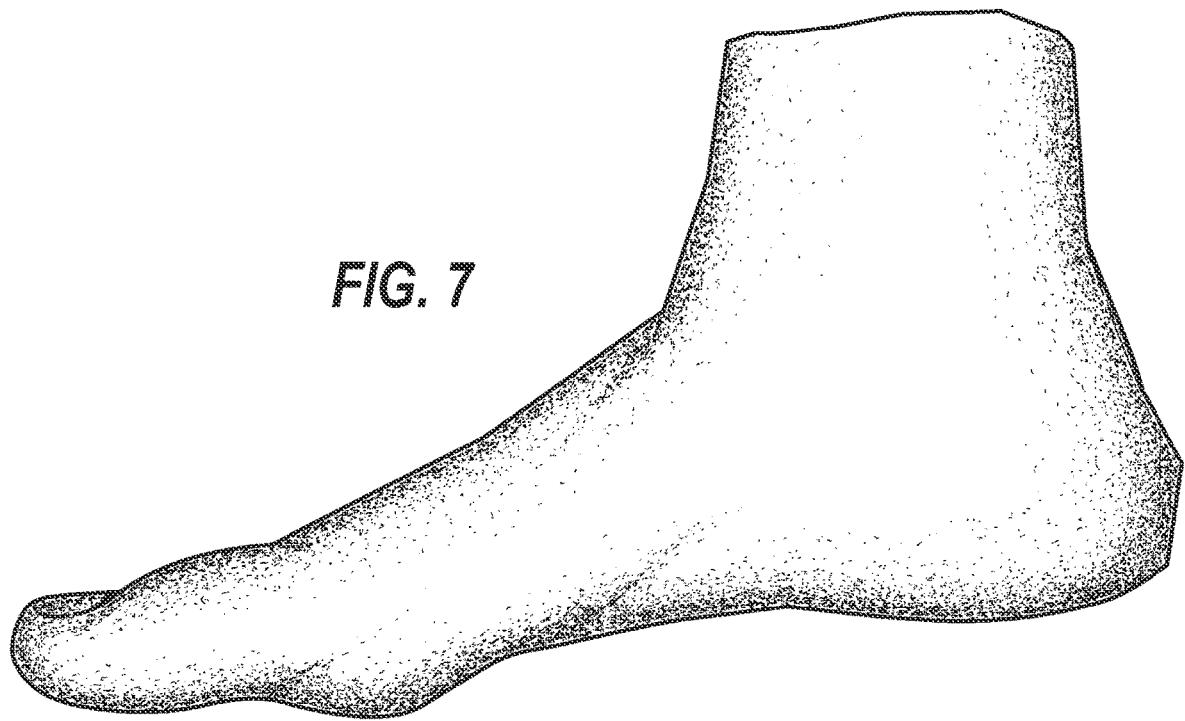
FIG. 7 illustrates an image of a foot captured by a 3D imaging apparatus.
Figure 8:
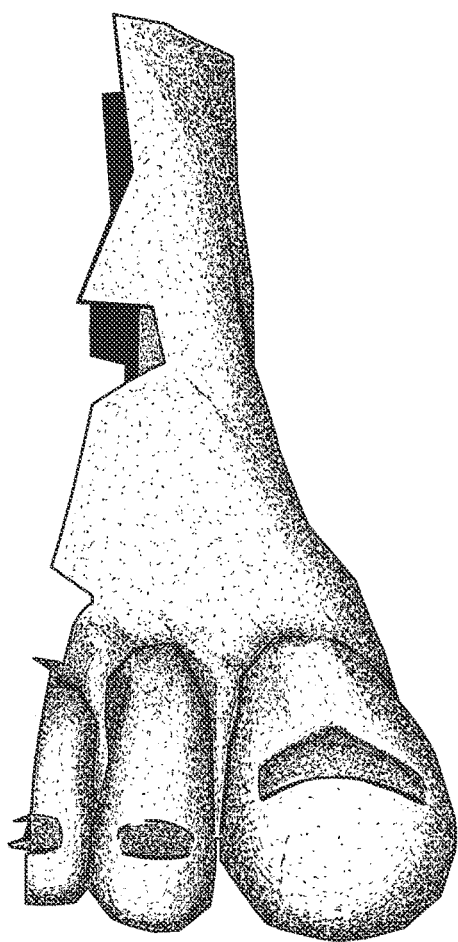
FIG. 8 illustrates the image of the foot rotated about an axis, showing that the other side of the foot has not been imaged.
Figure 9:
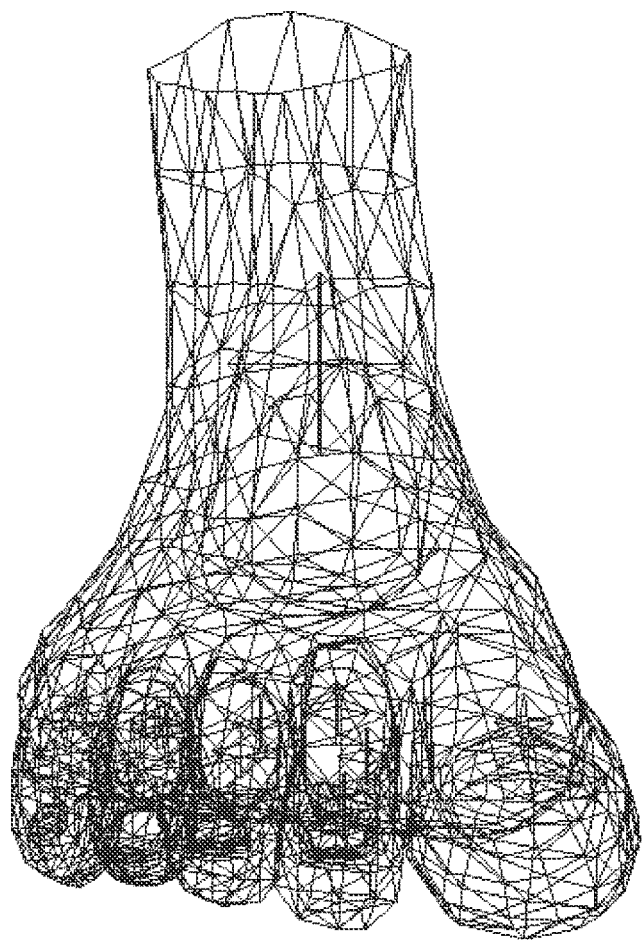
FIG. 9 illustrates a 3D model to be fitted to the 3D image data illustrated in FIG. 7.
Figure 10:
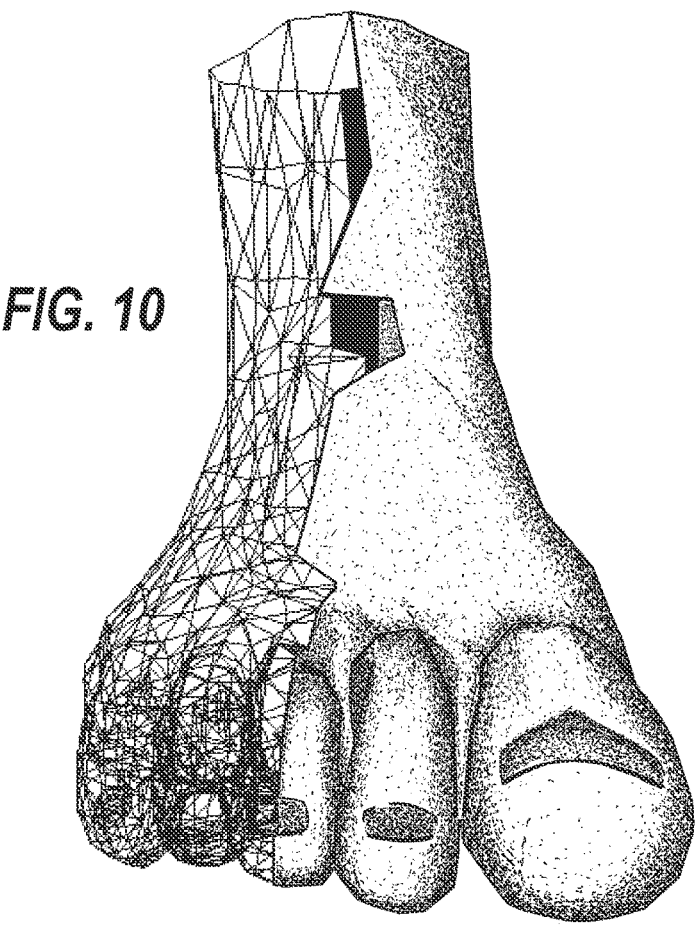
FIG. 10 illustrates the 3D model after it has been fitted to the captured 3D image data.

FIGS. 7 to 10 illustrates an example in which volumetric information is obtained using the techniques described herein when only part of the limb is visible to the depth sensing camera apparatus 102, 104. FIG. 7 illustrates a foot as presented to the 3D imaging system. FIG. 8 illustrates the image of the foot rotated about an axis, showing that the other side of the foot is completely missing in this view. FIG. 9 illustrates a 3D mesh model to be fitted to the 3D image data. FIG. 10 illustrates the 3D model as it has been fitted to the observed 3D image data. Thus, the extraction of full volumetric data from this 3D model is permitted even though only part of the limb is visible to the imaging system.

Figure 11:
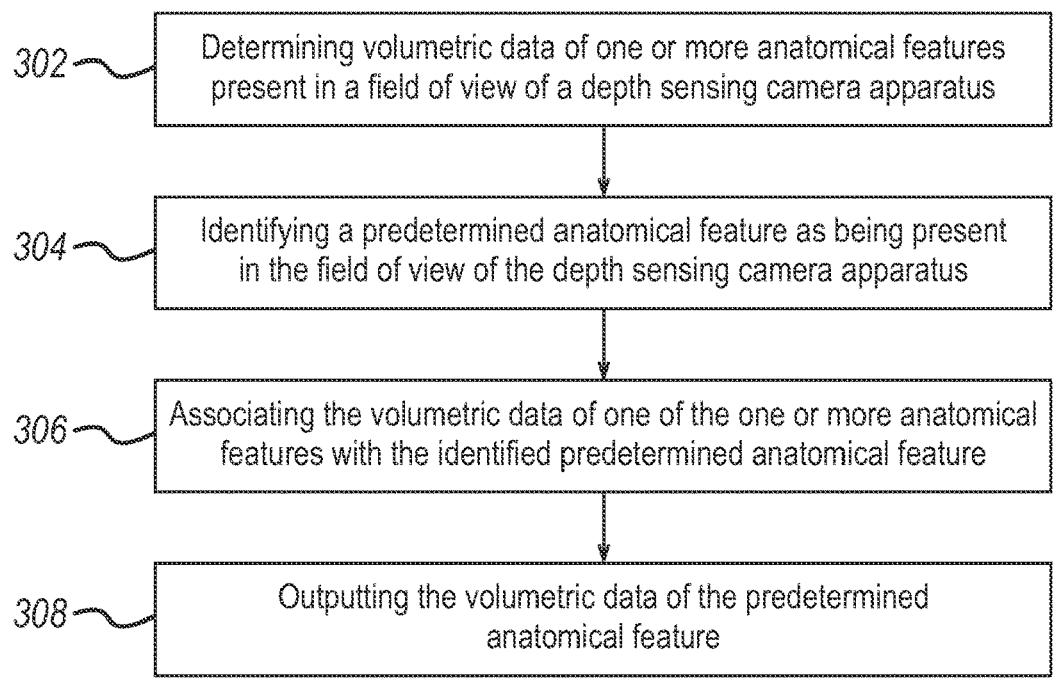
FIG. 11 illustrates a method according to an embodiment of the invention.

FIG. 11 illustrates a method of determining volumetric data of a predetermined anatomical feature according to an embodiment of the invention which may be performed by the processing device 108 or 110. Each of the steps may be performed in a different order (for example, step 304 may be performed before step 302), and may be omitted.

In step 302, volumetric data of one or more anatomical features present in a field of view of a depth sensing camera apparatus are determined.

In step 304, a predetermined anatomical feature is identified as being present in the field of view of the depth sensing camera apparatus.

In step 306, the volumetric data of one of the one or more anatomical features is associated with the identified predetermined anatomical feature.

In step 308, the volumetric data of the predetermined anatomical feature is output.

The apparatus 100 illustrated in FIG. 1 and described above, is capable of identifying not just a general limb of interest, but of identifying which among a corpus of possible limbs is currently in the field of view depth sensing camera apparatus. Thus, the apparatus could classify, for example, both the left and right feet of multiple occupants of a house provided that sufficient training data were available. In this way, the apparatus may trigger full 3D scanning only when one of the desired set of limbs of interest is within view. This also allows the apparatus to track multiple patients and/or limbs per patient.

In order to obtain clinically relevant volume measurements for edema detection, it is advantageous to obtain volumetric measurements with a precision of 5%, over a volume of around 2.5 liters, it is found that a dimensional accuracy of the order of 2.5 mm is required assuming equal errors in each dimension. Therefore, the apparatus described herein is capable of achieving at least 2.5 mm measurement resolution in each dimension for each pixel, and preferably better than 1 mm resolution in all 3 dimensions.

In an alternative embodiment, the reference 3D model may remain fixed, and a series of distortions are applied to the observed, point cloud 3D data to match the data the reference 3D model. Where references are made to distortions of the 3D model to match to the observed, the point cloud 3D data may be distorted via the inverse process to match the data the reference 3D model. Likewise, a further alternative embodiment could make adjustments to the 2D image data collected such that it matches the 3D model, or adjustments could be made to the 3D model and rendering techniques could then be used to match the observed 2D image data.

The applicant has found that it is possible to use 3D imaging systems with a resolution poorer than 2.5 mm throughout the scanning volume. However, this becomes increasingly reliant on the statistical distribution of multiple depth measurements at different points providing a correct "average" depth measurement, and thus providing an accurate match to a distortable 3D limb model. For example, fitting a low resolution point cloud to a higher resolution 3D model is possible by calculating the least-squares error in positions between points and the model. Adjusting a series of 3D model distortion parameters to minimize this least-squares error, assuming that each low-resolution point has independent errors associated, may result in a more reliable set of 3D model distortion parameters. However, it is apparent that as the measured points have increasingly poorer resolution, and particularly if the points do not have independent measurements between them, that this technique degrades rapidly. The applicant has found that this is the case, for example, when depth measurements are quantized as often happens as the result of stereo block matching algorithms in various categories of camera-based 3D scanners, or when many x,y points share the same depth information. Therefore, the apparatus described herein is configured to acquire image data with at least a 2.5 mm measurement resolution in at least two dimensions for each pixel, coupled with a model to statistically improve the resolution of the third dimension to better than 2.5 mm after processing.

In combination with the technical implementation provided above, involving the use of a full 3D model of the limb of interest including both orientation changes between the limb and camera apparatus as well as relative orientations between the joints in the limb, it becomes possible to use the "silhouette" technique to enable quantification of limb volume with respect to a detailed 3D model, by applying mathematical distortions to the model in order to match the observed high-resolution 2-dimensional imaging in dependence on the lower-resolution depth measurements. In this approach, the small quantization errors in depth measurement are effectively ignored, as the depth information is used to estimate the real-world area occupied by each observed pixel, and thus the real-world distance between pixels that make up the silhouette of the limb. For example, a 100 mm wide silhouette of an object as viewed by the camera at a distance of 1000 mm and an uncertainty of +/−10 mm in depth, yields an uncertainty in width of just +/−1 mm in the silhouette width. Therefore, provided that the 3D model is appropriately oriented and distorted to match the observed data, this silhouette data may overcome the depth-measuring errors to a large extent.

The acquired data has been typically described as being image data. However, if a known light source (e.g. a laser) and sensor array are used, it will be appreciated that the data are a representation of the distance from each pixel in the array to objections in the field of view or environment of the sensor array.

In a further embodiment, 3D image data is collected without first determining the presence of the feature (e.g. limb) of interest. This 3D image data is then processed as described previously to yield a 3D point cloud, against which a distortable model of the feature of interest is iteratively adjusted to maximize fit. It will be appreciated that at no stage here was an explicit recognition of the feature of interest performed, however in the case that the feature of interest is present, then the parameters of the distortable/deformable model will converge on meaningful values. However, implicit recognition of the feature of interest is possible, for example by setting allowable limits on parameter values for the model, or threshold levels on the quality of fit between the observed data and the 3D model. Therefore it will be understood that an implicit step of determining the presence or absence of the feature of interest may be performed after all 3D data capture and model fitting is complete. This may take the form of filtering the resulting model parameters (e.g. foot volume measurements) from a time-series of 3D image data, and retaining only data from those time-points that meet some data quality criteria. It will also be recognized that, rather than using an absolute threshold on data quality or the presence or absence of the feature of interest, it is possible to weight the results of the analysis by some measure of goodness-of-fit or calculated probability that the observations correspond to the feature of interest. In this way, feature recognition can be both implicit and fuzzy rather than a simple binary cut-off, and the accumulated results of analysis will tend to represent predominantly information from the feature of interest over multiple measurements.

A technique for obtaining the volume of a foot has been described. However, it will be appreciated that the technique may be applied to other limbs, or features (e.g. scars, wounds, etc.) of limbs, or any other anatomical feature or limb. Moreover, the technique described herein has focused on the use of measuring the volume of a foot, or feet for targeting heart failure. However, it will be appreciated that the technique may be used during pregnancy or for lymphoedema associated with breast cancer.

The embodiments described in accordance with the present invention may be provided as a computer software product. The computer software product may be provided in, on or supported by a computer readable medium which could be provided as all possible permanent and non-permanent forms of computer readable medium either transitory in nature, such as in a data transmission signal for example sent over the internet, or non-volatile storage such as memory. On the other hand the computer readable medium may be a non-transitory computer readable medium comprising all computer-readable media.

The term "computer readable medium" (or non-transitory computer readable medium) as used herein means any medium which can store instructions for use by or execution by a computer or other computing device including, but not limited to, a portable computer diskette, a hard disk drive (HDD), a random access memory (RAM), a read-only memory (ROM), an erasable programmable-read-only memory (EPROM) or flash memory, an optical disc such as a Compact Disc (CD), Digital Versatile Disc (DVD) or Blu-ray™ Disc, and a solid state storage device (e.g., NAND flash or synchronous dynamic RAM (SDRAM)). It will be appreciated that the foregoing discussion relates to particular embodiments. However, in other embodiments, various aspects and examples may be combined.

While the invention is described herein by way of example for several embodiments and illustrative drawings, those skilled in the art will recognize that the invention is not limited to the embodiments or drawings described. It should be understood, that the drawings and detailed description thereto are not intended to limit the invention to the particular form disclosed, but on the contrary, the intention is to cover all modifications, equivalents and alternatives falling within the spirit and scope of the present invention. The headings used herein are for organizational purposes only and are not meant to be used to limit the scope of the description. As used throughout this application, the word "may" is used in a permissive sense (i.e. meaning "might") rather than the mandatory sense (i.e., meaning "must"). Similarly, the words "include", "including", and "includes" mean including, but not limited to.

The following is a non-exhaustive list of embodiments which may be claimed:

1. A method of determining volumetric measurement data of a predetermined anatomical feature, the method comprising:

monitoring a field of view of a depth sensing camera apparatus;

identifying a predetermined anatomical feature as being present in the field of view of the depth sensing camera apparatus;

upon identification of the predetermined anatomical feature being present in the field of view of the depth camera apparatus, determining volumetric measurement data of the identified anatomical feature present in the field of view of the depth sensing camera apparatus; and outputting the volumetric measurement data of the predetermined anatomical feature.

2. The method of embodiment 1, the method comprising: upon identification of the predetermined anatomical feature being present in the field of view of the depth sensing camera apparatus, obtaining three-dimensional data of the predetermined anatomical feature and determining the volumetric measurement data of the predetermined anatomical feature based on the three-dimensional data, wherein the three-dimensional data comprises data acquired by the depth sensing camera apparatus, or depth measurement or point cloud data generated therefrom.

3. The method of embodiment 1 or embodiment 2, comprising acquiring a two-dimensional image from the depth sensing camera apparatus and identifying the predetermined anatomical feature as being present in a field of view of the depth sensing camera apparatus in accordance with the two-dimensional image.

4. A method of determining volumetric measurement data of a predetermined anatomical feature, the method comprising:

determining volumetric measurement data of one or more anatomical features present in the field of view of the depth sensing camera apparatus;

subsequently identifying one of the one or more anatomical features as being a predetermined anatomical feature; and outputting the volumetric measurement data of the one of the one or more anatomical features identified as the predetermined anatomical feature.

5. The method of embodiment 4, the method comprising: obtaining three-dimensional data of the one or more anatomical features and determining the volumetric measurement data of the one or more anatomical features based on the three-dimensional data, wherein the three-dimensional data comprises data acquired by the depth sensing camera apparatus, or depth measurement or point cloud data generated therefrom.

6. The method of embodiment 4 or embodiment 5, wherein the volumetric measurement data of one of the one or more features is associated with the identified predetermined anatomical feature by comparing the volumetric measurement data of each of the one or more anatomical features with a three-dimensional representation of a predetermined anatomical feature, and identifying one of the one or more anatomical features as being the predetermined anatomical feature.

7. The method of embodiment 2 or embodiment 5, wherein determining the volumetric measurement data comprises processing the three-dimensional data in dependence on a three-dimensional representation of the predetermined anatomical feature.

8. The method of embodiment 7, wherein the three-dimensional representation of the predetermined anatomical feature is a deformable three-dimensional model, and wherein the method comprises parametrically deforming the three-dimensional model to fit the three-dimensional data of the predetermined anatomical feature.

9. The method of embodiment 8, wherein the three-dimensional model is deformed by one or more of rotation, altering a joint angle and volumetric change.

10. The method of embodiment 7, wherein the three-dimensional representation of the predetermined anatomical feature is a deformable three-dimensional model, and wherein the method comprises deforming the three-dimensional data of the predetermined anatomical feature to fit the three-dimensional model.

11. The method of any one embodiments 2, 5, and 7 to 10, wherein the three-dimensional data comprises multiple data sets of anatomical features at different orientations.

12. The method of any one embodiments 2, 5, and 7 to 11, wherein data is periodically or continuously received from the depth sensing camera apparatus.

13. The method of any one embodiments 2, 5, and 7 to 12, wherein the three-dimensional data comprises three-dimensional image data.

14. The method of any one embodiments 2, 5, and 7 to 13, wherein the three-dimensional data represents at least one partial representation of the predetermined anatomical feature.

15. The method of any one embodiments 2, 5, and 7 to 14, comprising recording the time at which three-dimensional data is captured, and wherein the volumetric measurement data is generated in dependence on the recorded time.

16. The method of any of the preceding embodiments, wherein the predetermined anatomical feature is a limb, and is preferably a foot.

17. The method of any of the preceding embodiments, wherein the depth sensing camera apparatus comprises at least one emitter and one detector array, or at least two detector arrays.

18. A system comprising:
a depth sensing camera apparatus; and
a processor coupled to the depth sensing camera apparatus; wherein the processor is configured to perform the method according to any one of embodiments 1 to 16.

19. The system of embodiment 17, wherein the depth sensing camera apparatus comprises at least one emitter and one detector array, or at least two detector arrays.

20. A computer readable medium having stored thereon instructions which, when executed on a processor, cause the processor to perform the method according to any one of embodiments 1 to 16.

21. An method as substantially hereinbefore described with reference to the accompanying figures.

22. An apparatus as substantially hereinbefore described with reference to the accompanying figures.

The invention claimed is:

1. A method of determining volumetric data of a predetermined anatomical feature, the method comprising:
identifying one or more predetermined anatomical features as being present in a field of view of a three-dimensional imaging camera apparatus;
determining volumetric data of the one or more predetermined anatomical features present in the field of view of the three-dimensional imaging camera apparatus;
associating the volumetric data of at least one of the one or more predetermined anatomical features with the identified one or more predetermined anatomical features; and
outputting the volumetric data of the at least one of the said one or more predetermined anatomical features.

2. The method of claim 1, wherein the step of determining volumetric data further comprises:
estimating an outline of at least one of the one or more predetermined anatomical features in one or more images.

3. The method of claim 2, wherein the one or more images are two-dimensional images.

4. The method of claim 2, wherein the outline comprises at least one partial outline.

5. The method of claim 2, wherein the step of determining volumetric data further comprises either:
processing the outline using an estimate of a distance from a reference point to the at least one of the one or more predetermined anatomical features; or
processing the outline using an estimate of a distance from a reference point to one or more points on the outline.

6. The method of claim 2, wherein the step of determining volumetric data further comprises:
processing the outline using a three-dimensional representation of the at least one of the one or more predetermined anatomical features.

7. The method of claim 1, wherein the step of determining volumetric data further comprises:
utilizing a model that has been produced based on at least one representation of the one or more predetermined anatomical features.

8. The method of claim 1, wherein the three-dimensional imaging camera apparatus captures at least two spatial dimensions and a temporal dimension.

9. The method of claim 8, wherein the temporal dimension comprises a phase relationship between the three-dimensional imaging camera apparatus and a light emitting apparatus.

10. The method of claim 1, wherein the three-dimensional imaging camera apparatus captures at least two spatial dimensions from at least two viewpoints.

11. The method of claim 1, wherein the three-dimensional imaging camera apparatus captures at least two spatial dimensions in conjunction with a light emitting apparatus that differentially emits light in at least one spatial dimension and the temporal dimension, or in the at least two spatial dimensions.

12. The method of claim 1, wherein the three-dimensional imaging camera apparatus directly or indirectly captures at least three spatial dimensions.

13. The method of claim 1, wherein the step of identifying one or more predetermined anatomical features does not use an output of the three-dimensional imaging camera apparatus.

14. The method of claim 6, wherein the three-dimensional representation is a deformable three-dimensional model.

15. The method of claim 14, wherein the three-dimensional model is deformed by rotation, altering a joint angle, and/or volumetric change.

* * * * *